(12) United States Patent
DiFilippo et al.

(10) Patent No.: US 6,829,378 B2
(45) Date of Patent: Dec. 7, 2004

(54) REMOTE MEDICAL IMAGE ANALYSIS

(75) Inventors: Frank P. DiFilippo, Strongsville, OH (US); Arun Sivashankaran, San Francisco, CA (US); Stephen M. Behm, Avon, OH (US); Benjamin A. Cottrill, Cleveland Heights, OH (US)

(73) Assignee: Biomec, Inc., Cleveland, OH (US)

( * ) Notice: Subject to any disclaimer, the term of this patent is extended or adjusted under 35 U.S.C. 154(b) by 617 days.

(21) Appl. No.: 09/849,733

(22) Filed: May 4, 2001

(65) Prior Publication Data

US 2002/0164059 A1 Nov. 7, 2002

(51) Int. Cl.[7] .............................. G06K 9/00; A61B 5/00
(52) U.S. Cl. ....................................... 382/128; 600/300
(58) Field of Search ................................ 382/100, 128, 382/129–134, 305; 345/619; 358/1–15, 403; 378/198, 62; 600/300, 26, 437

(56) References Cited

U.S. PATENT DOCUMENTS

| | | | |
|---|---|---|---|
| 5,235,510 A | * 8/1993 | Yamada et al. | 600/300 |
| 5,321,520 A | * 6/1994 | Inga et al. | 358/403 |
| 5,579,393 A | 11/1996 | Conner et al. | 713/176 |
| 5,655,084 A | 8/1997 | Pinsky et al. | 705/3 |
| 5,807,256 A | * 9/1998 | Taguchi et al. | 600/425 |
| 5,851,186 A | 12/1998 | Wood et al. | 600/437 |
| 5,891,035 A | 4/1999 | Wood et al. | 600/437 |
| 5,897,498 A | 4/1999 | Canfield, II et al. | 600/437 |
| 5,938,607 A | 8/1999 | Jago et al. | 600/437 |
| 6,006,191 A | 12/1999 | DiRienzo | 705/2 |
| 6,018,713 A | 1/2000 | Coli et al. | 705/2 |
| 6,032,120 A | 2/2000 | Rock et al. | 705/2 |
| 6,260,021 B1 | * 7/2001 | Wong et al. | 705/2 |
| 6,381,029 B1 | * 4/2002 | Tipirneni | 358/1.14 |
| 6,501,849 B1 | * 12/2002 | Gupta et al. | 382/141 |

OTHER PUBLICATIONS

Banerjee, S.; "Multimedia Traffic Analysis and Control in a High–Speed Medical Communications Environment", University of Miami, Mar. 29–31, 1994, pp. 416–420.*
Kotsopoulos et al., "A New Data Management Concept in a Hybrid Cellular Mobile Radio Communication Network", University of Patras, Greece; IEEE 1991, pp. 674–680.*
Sudhakar et al., "Design and Performance Evaluation Considerations of a Multimedia Medical Database", IEEE Transactions, Knowledge and Data Engineering, Oct. 1993, pp. 888–894.*
Aaron Berez, M.D.; "OsteoNet receives Advanced Technology Program grant from the National Institute of Standards and Technology"; Oct. 4, 2000; <http://www.osteonet.com>.

* cited by examiner

Primary Examiner—Jayanti K. Patel
(74) Attorney, Agent, or Firm—Pearne & Gordon LLP

(57) ABSTRACT

The Remote Medical Image Analysis System implements a process for providing computerized medical image analysis for medical service providers using an Application Service Provider [ASP] model. To analyze a medical image, the system accepts a medical image file from a remotely located user. The medical image file is transferred over a computer network, such as the Internet, wherein the system analyzes the medical image file. The analysis results (which may include transformed images, reports, and diagnoses) are then transferred by the system to the user over the computer network. To accomplish this task, the system implements web servers, application servers, and processing servers, with data servers utilizing a database for data storage and retrieval, coordinating data flows among the various servers and system users and archiving data for longer-term storage.

20 Claims, 4 Drawing Sheets

REMOTE MEDICAL IMAGE ANALYSIS

This invention was made with Government support under Grant No. 1R43-NS39207-01 awarded by the National Institutes of Health. The licensee acknowledges that the U.S. Government has certain rights in this invention under 37 C.F.R. §401 including a non-exclusive, non-transferable, irrevocable, paid-up license in this invention and the right in limited circumstances to require the patent owner to license others on reasonable terms as provided for by the terms of the above identified grant awarded by the National Institutes of Health.

BACKGROUND OF THE INVENTION

The invention generally relates to a medical imaging processing and analysis system, and, more particularly, to a computerized medical imaging processing and analysis process and system capable of remotely analyzing a medical image.

Medical imaging and analysis is becoming critical to the medical diagnosis and treatment of many different diseases and disorders. Such medical imaging started with the ubiquitous X-ray photograph, and today includes CT and MRI imaging, among other technologies. Medical imaging technologies are being developed and improved all the time. These imaging technologies allow complex images of the internal organs of a human being to be captured, often in three dimensions and in complex detail. For instance, medical imaging has proven especially useful in the diagnosis and treatment of brain diseases, including Multiple Sclerosis, Alzheimer's, and Parkinson's, among others.

Because these medical images can be so extremely detailed and complex, medical care practitioners have sought new technologies to help them evaluate and interpret these medical images. Thus, computer systems utilizing complex software to aid in the interpretation and diagnosis of medical images are being developed at a rapid pace.

These new medical imaging computer systems implement breakthroughs in digital imaging technology and computer processing capabilities. Utilizing these new technologies, the imaging systems are useful to aid medical practitioners by enhancing important aspects of a medical image, eliminating superfluous detail, and even by providing preliminary medical diagnoses. Also, these imaging technologies are being adapted to help understand the functioning of human organs, including the human brain.

However, advances in the medical profession are occurring at ever increasing rates. Meanwhile, the costs of these technologies continue to rise. The confluence of these circumstances means that medical facilities must allocate ever increasing portions of their cash flow to modernizing and updating their equipment. If a medical provider is to utilize the most recent advances in medical imaging, it is typically required to regularly purchase ever faster computers and install ever more complex software to stay abreast of the latest advances. The rapid pace of advancement in the technology requires that this software be updated regularly. And the limited use of these imaging systems means that it is difficult to recover the costs associated with them. These issues put a severe drain on the monetary resources of medical providers, preventing these investment dollars from being used for other purposes or prohibiting some medical providers from making such imaging diagnosis tools available to their patients.

An alternative service paradigm for providing medical imaging services that allows for nearly continuous upgrades and advances in capabilities without requiring substantial up-front or continuous monetary investment in the latest imaging analysis technologies would be very beneficial to the medical provider community.

Such a service paradigm can utilize the Application Service Provider [ASP] business model. The ASP model allows software to be installed and maintained on powerful and/or special purpose computers and/or utilize parallel processing. A service is then provided whereby remotely located users can access these programs from their own computers, such as, for example, via the Internet. Data is exchanged between the user and the ASP, but the ASP computers and software do the actual processing of the data. Thus, users can utilize powerful and complex hardware/software solutions without being required to make the financial investment in purchasing and maintaining the computer systems and software. In turn, the ASP can make a profit by selling the computer services to remotely located users. In this way the ASP model can help to maximize the utilization of computing resources.

More specifically, ASPs provide a contractual service offering to deploy, host, manage, and rent access to an application from a centrally managed facility. This allows providing software functionality to become an ongoing service, instead of a shrink-wrapped product, creating a longer lasting relationship with the customer. Deploying software in this manner allows the service provider to immediately introduce new revenue-generating features, capitalize on third party advertising, and rapidly expand the customer base through "viral-marketing" techniques. Several important characteristics define ASPs, including:

Application Centricity: Unlike basic hosting services, which focus on the management of the network and connectivity, or business processing outsourcing, which manages an entire process such as accounting or human resources, ASPs provide access to and management of a commercially available application.

"Renting" Application Access: By saving the users from making up-front investments in software licenses, personnel, or equipment, ASP providers offer access to users on a per-use or subscription basis.

Central Management: By helping the users avoid the many issues of software use at individual sites, including loading the software on different computers of different configuration, troubleshooting problems at numerous sites, and updating with new versions, ASPs allow complete management of the software from the provider's end, without involvement of the user.

ASPs, in particular, allow multiple users to take advantage of a single software solution to a particular problem. Therefore, once a software solution is created for an individual problem, other users can immediately take advantage of it without having to duplicate the efforts and costs of the original developers. Thus, the ASP model creates a one-to-many relationship (one application shared among many users), with significant cost savings over the traditional methods of software deployment.

The Remote Medical Image Analysis System utilizes a business model similar to the ASP paradigm to the medical community, offering remotely located doctors, clinicians, researchers, and other medical providers new, up-to-date medical software imaging tools using a fee-for-service ASP model, with fees charged either on a pay-per-use (e.g., credit card) or on a subscription basis. For example, one early anticipated use of the invention is the quantification of brain atrophy for Multiple Sclerosis patients.

Additional uses in addition to the above-mentioned brain atrophy measurement can involve other medical imaging modalities besides magnetic resonance, such as planar x-ray, x-ray computed tomography (CT), positron emission tomography (PET), single photon emission computed tomography (SPECT), ultrasound, optical imaging, and electromagnetic biomedical signals. Also, the region of interest is not limited to the brain. The Medical Image Analysis System can thus provide medical practitioners with access to state-of-the-art medical image analysis capability at little or no initial investment by the user.

The ASP model can support the growing list of medical imaging software programs (beyond those described above) as such programs are developed. Parallel processing capability can also be easily implement by an ASP, allowing for more efficient image processing and more complex application support, allowing users to benefit from the parallel processing capability of an ASP without the expense of implementing such a system. Thus, the Remote Medical Image processing System can be a useful means of providing complex medical imaging technology to various medical providers in a beneficial and cost effective way.

SUMMARY OF THE INVENTION

The Remote Medical Image Analysis System implements a process for providing computerized medical image analysis for medical service providers.

To analyze a medical image, the networked system accepts a medical image file from a remotely located user. The medical image file is transferred over a computer network using computer operations. The system then analyzes the medical image file also via computer operations. The analysis results (which may include transformed images, reports, and diagnoses) are then transferred by the system to the user, again via computer operations over the computer network.

DETAILED DESCRIPTION OF THE INVENTION

Figure 1:
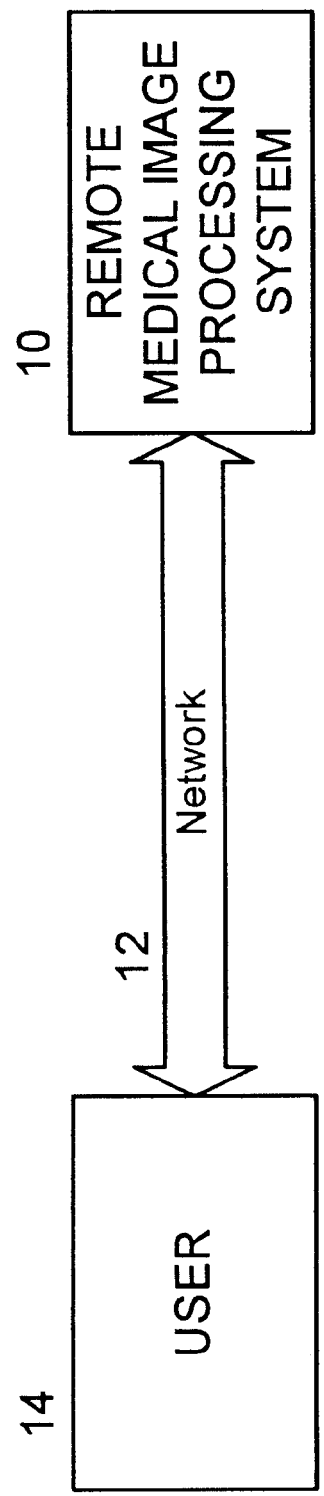
FIG. 1 is a block diagram showing the system interacting with a user.

FIG. 1 shows the basic structure of the remote medical analysis system 10. The system 10 is connected to a user 14 via a network 12. The user can be, and typically will be, remotely located, but in some cases may be co-located with the system 10. This system implements the remote medical image analysis as defined herein.

The user will typically access the system by using a computer local to the user. Any computer network 12 can be utilized for providing the user 14 the ability to use a computer to remotely access the system 10. Because of the ubiquitous nature of the Internet, it is anticipated that the Internet will be an effective means to implement the computer network 12. Alternative means to implement the computer network also include other Wide Area Networks (WANs) such as corporate or private intranets. Local Area Networks (LANs) can also be used, especially when the user is located near the system 10, such as where the user is located in geographically close proximity to the system 10. Finally, dedicated lines or even dial-up accounts (e.g., modems) could also be utilized for implementing the network 12. For example, users expecting to heavily use the system may want a dedicated network connection to the system (such as a T1, DSL, LAN, ISDN, or some similar network solution). Alternatively, very remotely located users may need a custom means of connecting the user to the system. Dial-up connections, or perhaps even wireless connections are alternatives within the scope of the invention.

To summarize the operation of the system, once the user 14 is connected to the system via the network 12, the user 14 can transfer a medical image file from the user's location to the system 10. The system 10 will then analyze the medical image file, and then return results to the user 14 via the network 12.

Figure 2:
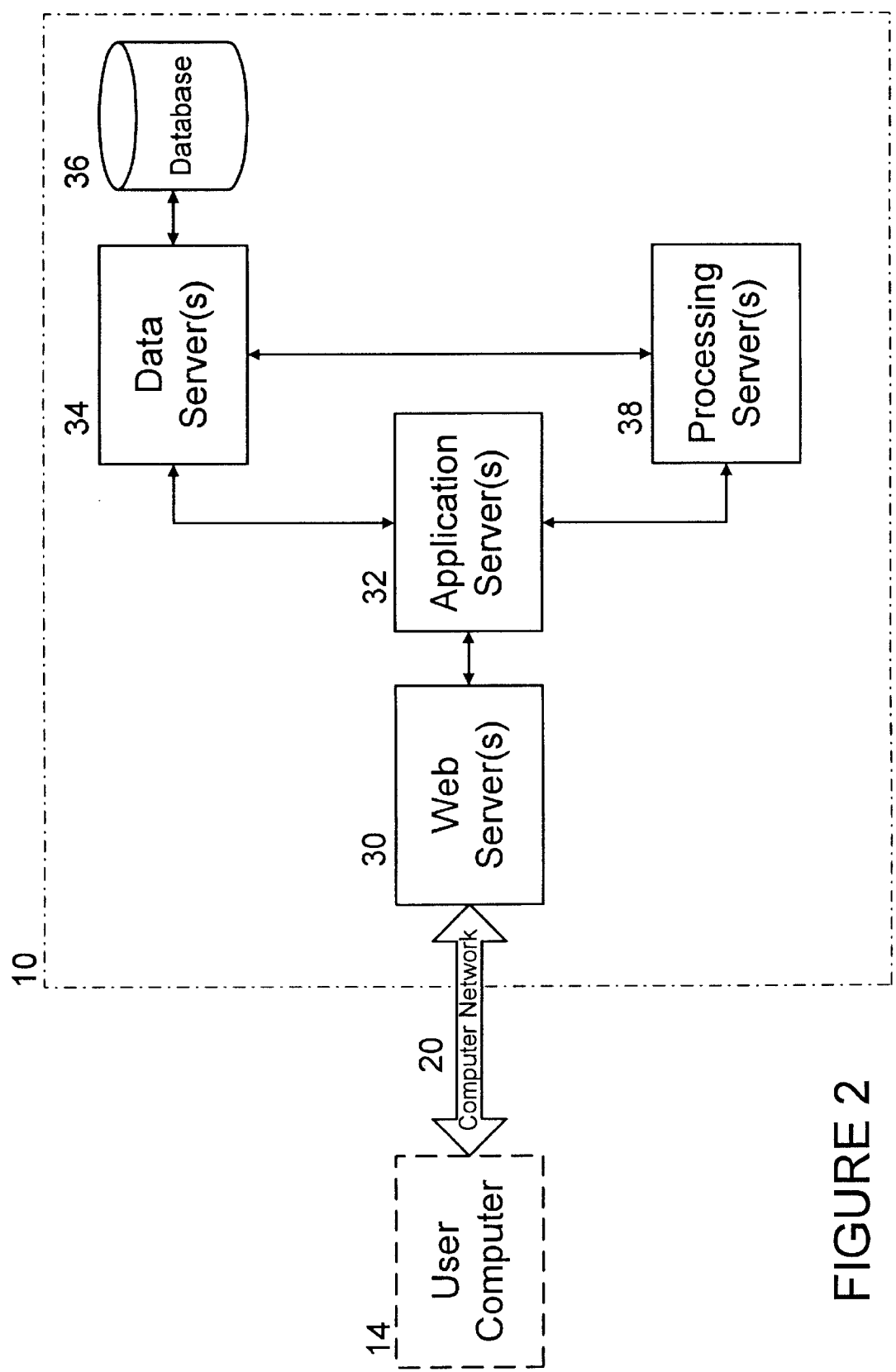
FIG. 2 is a block diagram showing the major components of the system interacting with the user and with each other.

FIG. 2 shows a typical system configuration for remote analysis of medical images. The user computer 16 connects to the system 10 via a computer network 12.

The network 12, as described above, would typically be a WAN, such as the Internet or an intranet, although other computer networks can be used, depending on the needs of the user.

The system 10 will contain a web server 30 to interact with multiple users. The web server 30 will be the primary interface between the user and the system. The web server can utilize the HTTP protocol using HTML, for example, to exchange information between the user and the system, so that a user can interact with the system using an industry standard web browser. Additional interactive capability can be provided by utilizing dynamic page generation capability provided by any of a number of different applications and protocols, including HTML and dynamic HTML, XML, Active Server pages, Java Server pages, Java or Java scripting, iHTML, CGI scripting, or any other similar technology, which can be integrated into the web server platform.

The web server may be physically implemented by running a web server application on a stand-alone computer, or it may run on hardware shared with other applications. Further, the web server may be distributed across multiple machines, or be multi-homed, in order to meet heavy demand by multiple users.

Although the web server will provide the primary interface between the system and the users, other systems may interact directly with the user in order to increase the efficiency of the system operation over the computer network. For example, the image file and analysis results transfer operations (described hereinbelow) may bypass the web server in order to speed up the transfer process. Thus, this transfer could utilize other transfer protocols besides HTTP, such as FTP, for example. Security via data encryption, which is often a concern for medical images, can be implemented using the HTTPS protocol, or other similar protocols.

The web server 30 will provide information obtained from the user (described in more detail hereinbelow) to the application server 32. The application server 32 will parse the information provided by the user to the appropriate application. For example, some information will be sent to the data server(s) 34 to be saved in a database 36. There may be more than one data server 34, or multiple databases 36, depending on the bandwidth of the data to be saved, and the anticipated load on the system.

Other information will be sent by the application server 32 to the processing server or servers 38. The processing servers 38 will run the actual medical imaging applications that analyze the medical images. There may be a separate software application for each type of analysis to be done, or a single application may be able to perform multiple analyses. Each separate imaging application may run on a separate computer, or multiple applications may run on a single computer. In addition, multiple instances of applications utilized more often by users may be set up to increase productivity and efficiency.

The processing servers 38 will share information with the data servers 34. For example, processing information collected by the user can be stored in by the data servers 34 and provided to the processing servers 38 as needed. In addition, the analysis results will be provided by the application servers 38 to the data servers 34 for storage and/or archiving in the database 36. Data communication between the servers can be based on the XML language, which is rapidly emerging as an Internet standard.

The processing server(s) 38 are the heart of the medical imaging system. The image analysis and processing software will reside on one or more processing servers 38. This imaging software could be custom designed, licensed from third parties, or even commercially available software. Multiple software programs may be utilized together in order to fully analyze the medical images, and provide the user with a wealth of analysis results. The image analysis software may allow the user to specify certain analysis or processing parameters in order to enhance the image analysis processing function. By adjusting these parameters, the medical user may be able to enhance the analysis process.

The image analysis software may include the ability to transform the medical images provided by the users, creating enhanced images which may include highlighting, coloring, emphasis or de-emphasis of detail, digital filtering, among many other potential transformations. The image analysis software may also generate diagnoses and/or reports based on the analysis of the medical image. Further, the software could be designed to generate recommendations to the user to adjust analysis parameters for additional analyses, which might result in a better diagnosis or more enhanced transformed images. Additional examples of products of the image transformation and analysis process include:

- Numerical measures (for example, for brain atrophy the system can provide a number describing the ratio of brain volume to outer contour volume);
- Statistical measures (such as a diagnostic probability compared to patient data accumulated in a database);
- Highlighted images (such as the original images enhanced with outlines or colored regions delineating areas of interest); and
- Processed images (new images created through processing of the original images).

One embodiment of this system utilizes image analysis software to perform brain atrophy measurements from magnetic resonance images, for example, for assessing the progression of neurological diseases such as Multiple Sclerosis or Alzheimer's Disease. The invention will allow this software to be utilized more efficiently, and allow its use by a larger number of users, than is currently the case.

The system can also utilize various image analysis software packages, since the platform software will be designed in a modular fashion, accepting "plug-in" applications for various image analysis tasks. Users can then select the desired analysis task from a menu of choices. Processing tasks in addition to the above-mentioned brain atrophy measurement can involve other medical imaging modalities besides magnetic resonance, such as planar x-ray, x-ray computed tomography (CT), positron emission tomography (PET), single photon emission computed tomography (SPECT), ultrasound, optical imaging, and electromagnetic biomedical signals. Also, the region of interest is not limited to the brain.

Figure 3:
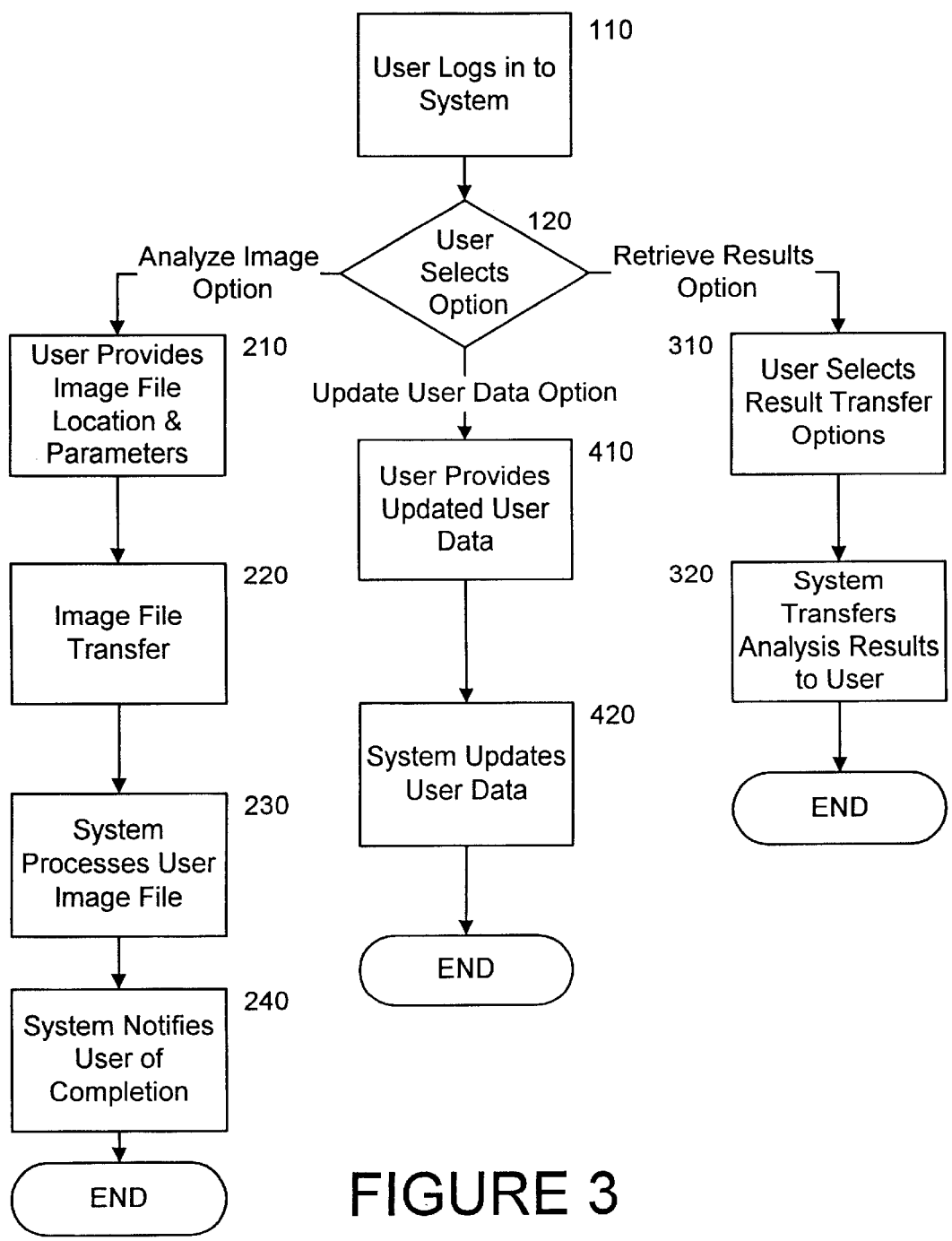
FIG. 3 is a flow chart showing the high-level operation of the system.

FIG. 3 is a flow chart of the basic process and operation of one possible implementation of the system shown in FIG. 2 and described above. In the preferred implementation, the Internet is used as the computer network, using the web server(s) 30 utilizing the HTTP or HTTPS protocol for most user interactions, although other computer networks and communication protocols could also be utilized. Under this implementation, when a user wants access to the system, the user uses a web browser to access the system web server 30. The system will respond, for example, by generating web pages with some basic information, and with a login option, represented by step 110, and transmitting these information pages and prompts to the user over the network.

To ensure that the system is secure, the user should have a previously set-up user identification (ID) and password to have access to the system. The user may also be required to have previously negotiated some financial agreement to access the system to obtain the user ID and password.

As part of the login process 110, the web server 30 will authenticate the user ID and password by checking the user-provided login information against the ID and password information stored in the system database 36, and thus the system verifies that the user has provided the correct information. The system then notifies the user that the login is complete. If the user is not authorized to access the system, or only has limited access, then the user will be so notified, and accordingly prevented from having access beyond that permitted by the system.

After the user has successfully logged in, the system will prompt the user to select one of one or more options, as represented by step 120. Some of the possible options for the user to select include, for example:

- Analyze a medical image (or re-analyze a previously processed image);
- Update User Data; and
- Retrieve the Results of a medical image analysis;

This list is not exhaustive, as other options can be added as the system expands in the services it can offer users. After completing his session, the user can log off of the system, or the system may automatically log the user off the system after some time period of inactivity, whereby the user must again log on in order to obtain further access to the system. The steps for processing each of these options are described below:

Analyze a Medical Image: If the user selects the option of analyzing a medical image file (as part of step 120 in FIG. 3), the user is prompted to select the type of medical image processing/analysis to be performed, especially if the system offers more than one analysis option. The type of processing may depend on the type or content of the image (e.g., a brain MRI scan or a CT scan of the heart), and the disease being analyzed (e.g., multiple sclerosis or heart disease). As the system is expanded to include additional analysis capability, this list of options will also expand.

The user is also prompted, to provide processing parameters and file information, which the user can then enter into the system (step 210). The required information includes the location of the image file (which can be quite large), a job identifier (job ID) to identify this specific job (perhaps by patient name, or ID number), processing parameters that might be used to tell the system "how" to process the image (and which depend on the type of image processing to be performed), among other information.

After the processing parameters and user information is provided to the system, the image file is then transferred from the location provided by the user to the system. The system may use resources on the user's local machine to perform part of the file retrieval operation (such as utilizing functionality of the browser, for example). The image file, along with the processing parameters and any other information provided by the user, is transferred through the web server(s) 30 and, via the application server(s) 32, the image file is handed off to the data server(s) 34, and thereby stored in a database 36. The data server(s) 34 also ensures that the transferred data is linked to the user ID, and the job ID, so that the data is all associated with this particular user processing request.

According to step 230 of the flow chart of FIG. 3, the processing of the image file can then begin or be scheduled for a future time. The application server(s) 32 provides the appropriate processing server 38 with the necessary information in order to immediately begin, or, if necessary, schedule for a later time, the processing and analysis of the medical image according to the user selected option(s). The appropriate processing server 38 is chosen according to the installed image processing software, so that the requested analysis can be performed. Multiple processing selections may require multiple processing servers to be utilized. The chosen processing server(s) 38 can then obtain all of the necessary processing parameters as well as the image file directly from the database 34 via the database server(s) 34.

The system might be set up to prompt the user for additional information to complete a scheduled image analysis, should such information be found necessary during an initial analysis. Such prompting could be accomplished by notifying the user via email, instant messaging, or some other means. The user might then log into the system to provide such information, or perhaps provide such information via email, instant messaging, or some other means.

When the processing and analysis of the image file by the processing server(s) 38 is complete, the analysis results, which could include a transformed image, diagnoses, analysis reports, and other information resulting from the processing of the image file, are then stored in the database 36 via the data server(s) 34 for later retrieval by the user, and even for archiving of the data (which could be an additional service provided the user for a fee). In addition, the processing server may generate a re-analysis report that suggests running an analysis again. The processing server(s) 38 might also generate new processing parameters suggested for use by the re-analysis, such as in a re-run report, as part of the analysis results. This information can also be stored in the database 36 as outlined above.

Step 240 of the flow chart in FIG. 3 represents the system notifying the user that the analysis and file processing is complete, and ready for retrieval. This notification could be via email, instant messaging, or some other means of notification. Alternatively, or additionally, the user can be notified the next time that the user logs into the system.

In order to retrieve the completed analysis results, the user must again log into the system (step 110 of FIG. 3). After logging in, the user can select the Retrieve Results Option, discussed below, to retrieve the results of the medical image analysis.

As part of this processing option, or perhaps as an additional option, the user can select an option to re-process and re-analyze a previously processed file. This re-analysis may be accompanied by a request by the system for a modification of the processing parameters originally provided by the user. Alternatively, the system may provide recommended processing parameters, said parameters possibly provided as part of a "re-run" report, chosen to enhance the processing and analysis function, which the user could then accept or override with his own parameters.

Retrieve Results Option: If the user selects the Retrieve results option after appropriately logging into the system (described hereinabove), the system would then provide the user with information about medical imaging processing results that are available for retrieval (such as a listing of reports and/or images resulting from the analysis). Because the user may have run multiple medical image analyses, the system might give the user a list of available results for all recent analyses. The system might also make available a list of archived analyses that are still stored in the database, if any. The user can then select the desired analysis for viewing or retrieval (step 310 of FIG. 3). This request is transmitted, via the web server(s) 30, to the application server(s) 32, which can then retrieve the appropriate information from the database 36 via the data server(s) 34 (step 320 of FIG. 3).

The system may offer an option for the user to directly view the results (such as using a web browser), or some portion of the results (the transformed or highlighted image, reports, diagnoses, among others). The system may allow the user to toggle between the various reports and other analysis results as an expanded feature. Alternatively or additionally, the system may offer an option to transfer these results to the user computer for storage and later viewing.

Update Client Data: The user may find it necessary to update certain information from time-to-time. The system can provide an option to allow the user to update this information from the user option interface. For example, the user may want to update financial or payment information, address or phone numbers, email, credit card numbers, account numbers, patient information, job information (e.g., image analyses), or other information. Alternatively, the system could prompt the user for this information each time the user accesses the system, or chooses an option. Step 120 in FIG. 3 shows a system option which allows the user to choose to update this information, such as via a web browser, once the user is logged on. The user provides the requested information (step 410), and the system then updates that information.

Additional options may also be provided by the invention, depending on the actual processing algorithms implemented, and the needs of particular users. However, these additional options are inherent in the design of the system, which is quite flexible in its implementation. Expansion can be accomplished by adding processing servers 38, or installing additional applications in existing processing servers. The application servers 32 and web servers 30 are then easily updated to add the additional functionality. The basic procedures outlined above will still be applicable.

Figure 4:
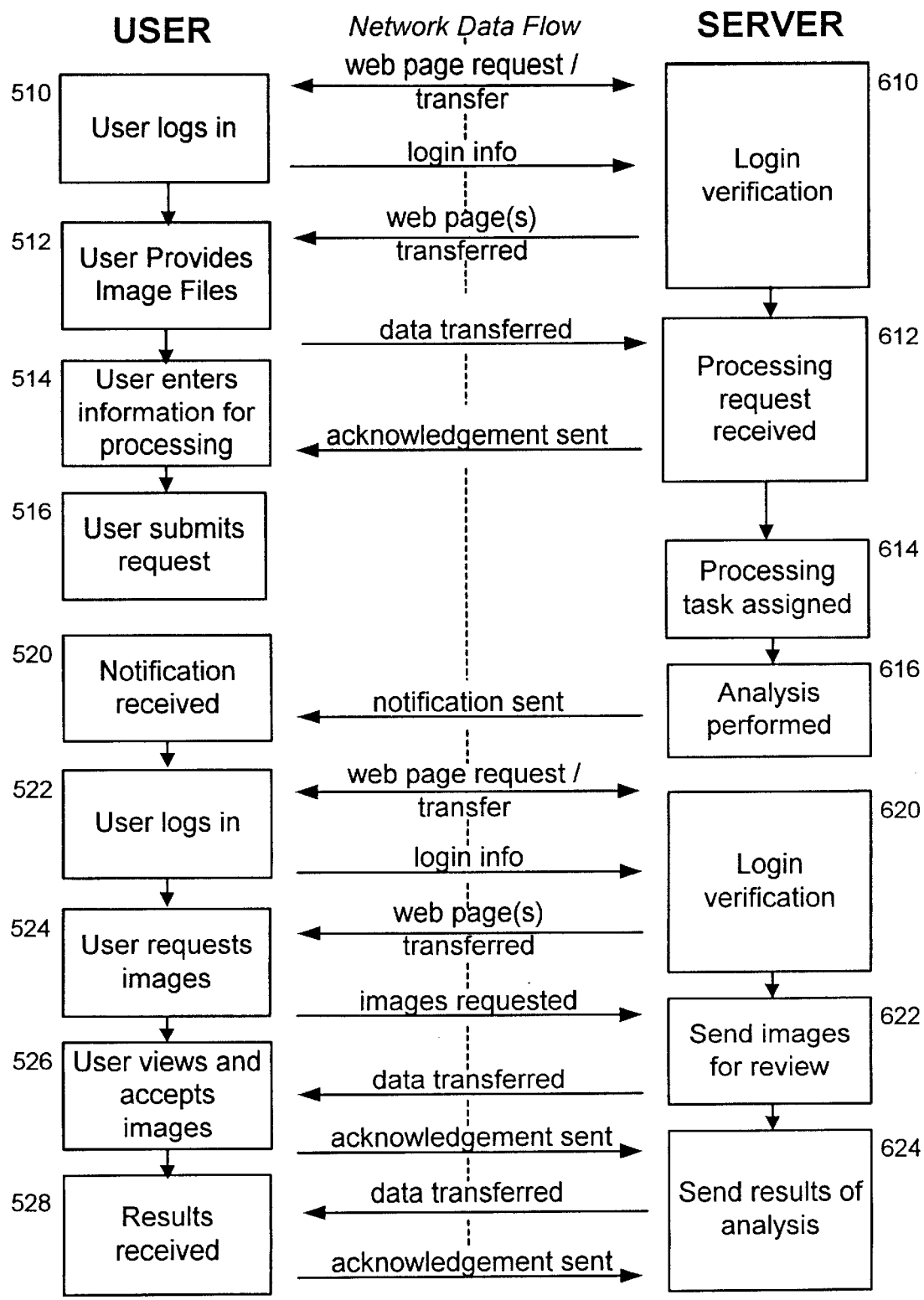
FIG. 4 is a flow chart showing a high-level data flow between the system and a user for analyzing an image file.

FIG. 4 shows the image file analysis process in more detail, the steps of which will be described in detail below:

After the client user contacts the system (such as by using the system domain name in a web browser), the system provides a login dialog with the user. The user logs in (510) by transferring login information to the system, which then verifies the user (610) and permits access if the user is authorized to have access.

Once the user is logged in, the system provides the user with data via web pages. The user then requests image processing, and the user also provides the medical image information (512) so that the image file can be transferred over to the system (612). The system also requests information and/or parameters necessary for processing and acknowledges receipt of the image file. The user then provides the requested information (514) and submits a request for final processing (516).

The system will then schedule the processing task (614), and when processing time is available, process and analyze the image file (616). The system then notifies the user that the analysis is complete (such as via e-mail or instant messaging).

Whether or not the user receives the notification (520), the user can again log on to the system (522), whereby the system will again verify the user (620). Once verified, the user can request to view the results of the analysis (images and/or reports) (524), wherein the system allows the display of these results (622). The user can view, and accept the results (526) and/or request that the results be transferred to the user computer, wherein the system will send the results (624) to the user (528). The system can also archive the results for future retrieval, or as a further service to the user.

The medical imaging analysis system charges the user for the processing and analysis operations performed. There are a number of different payment schemes that can be implemented in accordance with the invention, some of which can utilize an automated billing process. For example, the user might have an account set up in advance whereby the user is billed directly for the services on a regular basis, or the user's bank account can be debited via an automated electronic process. Alternatively, a user might provide a credit card number, or utilize some Internet payment scheme to pay for the services on an as-used basis, which can also be automated electronically. Or a user might pre-pay for the services. Any of these payment schemes, or all of them, among others, can be utilized to make a pay-for-service system that is flexible and responsive to the needs of the user. This business model allows the invention to be implemented similar to the ASP model as described above, to the benefit of medical service providers.

The invention has been described hereinabove using specific examples; however, it will be understood by those skilled in the art that various alternatives may be used and equivalents may be substituted for elements or steps described herein, without deviating from the scope of the invention. Modifications may be necessary to adapt the invention to a particular situation or to particular needs without departing from the scope of the invention. It is intended that the invention not be limited to the particular implementation described herein, but that the claims be given their broadest interpretation to cover all embodiments, literal or equivalent, covered thereby.

What is claimed is:

1. A process of providing a computerized medical image analysis system comprising the steps of:
   (I) prompting a user to select a system option, said prompting comprising the steps of:
      (A) providing the user with a set of system options for processing said medical image, said system options comprising:
         (i) an image analysis request; and
         (ii) an analysis results retrieval request;
      (B) requesting that the user select at least one of said system options; and
      (C) accepting said user selected system options;
   (II) analyzing a medical image file if the user selected said image analysis request, said analyzing comprising the steps of:
      (A) requesting that the user provide medical image information, said image information comprising:
         (i) a location of a medical image file;
         (ii) a job identifier; and
         (iii) processing parameters for analyzing said image file;
      (B) processing said medical image information, said processing comprising the steps of:
         (i) saving said medical image information in a database; and
         (ii) transferring said medical image file to said database, wherein said medical image file is obtained from said location of said medical image file;
      (C) analyzing said medical image file, said analyzing comprising the steps of:
         (i) transforming said image file, wherein said transforming creates a transformed image file;
         (ii) storing said transformed image file in said database, wherein said transformed image file is linked to said job identifier;
         (iii) generating an analysis report, wherein said analysis report contains a medical interpretation of said transformed image file; and
         (iv) storing said analysis report in said database wherein said analysis report is linked to said job identifier; and
      (D) notifying the user that said analysis is complete;
   (III) transferring analysis results to the user if the user selected said analysis results retrieval request, said transferring comprising the steps of:
      (A) requesting analysis results retrieval transfer information from the user, said analysis results retrieval transfer information comprising:
         (i) a job identifier; and
         (ii) an transfer options list, wherein the user can select one or more transfer options from said transfer options list;
      (B) accepting the analysis results retrieval transfer information provided by the user;
      (C) performing an analysis results transfer to the user.

2. The process of claim 1 further comprising the steps of:
   (I) processing a user login request, said login request comprising the steps of:
      (A) providing the user with a login prompt;
      (B) accepting a user login input; and
      (C) processing the user login input;
   (II) allowing the user to log off said medical imaging system; and further wherein said notifying the user that said analysis is complete can occur either when the user is logged on or when the user is logged off the system.

3. The process of claim 2 wherein said notifying the user that said analysis is complete is done by using email.

4. The process of claim 1, wherein:
   (I) said analyzing of said medical image file further comprises the steps of:
      (A) generating a re-run report, wherein said re-run report contains suggested modifications to said processing parameters for a re-analysis of said medical image file; and
      (B) storing said re-run report in said database, wherein said re-run report is linked to said job identifier;
   (II) said providing the user with a set of system options for processing said medical image further comprises the step of notifying the user of a suggested re-analysis of said medical image file if said re-run report recommends a re-analysis.
   (III) said providing the user with a set of system options for processing said medical image further comprises an image re-analysis request; and further comprising the step of:

(IV) re-analyzing said medical image file if the user selected said re-analysis request, said re-analyzing comprising the steps of:
  (A) prompting the user for the job identifier of the medical image to be re-analyzed;
  (B) accepting the updated job identifier input by the user;
  (C) prompting the user for an update to said processing parameters;
  (D) accepting the updated processing parameters from the user;
  (E) re-processing said medical image information, said re-processing comprising the steps of:
    (i) linking said medical image parameters and said medical image file to an updated job identifier; and
    (ii) linking said updated job identifier to said user ID;
  (F) analyzing said medical image file; and
  (G) notifying the user that said re-analysis is complete; and
(V) transferring re-analysis results to the user if the user selected said analysis results retrieval request.

5. The process of claim 4 wherein:
(I) said providing the user with a set of system options for processing said medical image further includes the option of allowing a user to choose a user information update request; and
(II) further comprising the step of performing a user information update request if the user selected said user information update request.

6. The process of claim 1 further comprising the steps of:
(I) processing a user login request, said login request comprising the steps of:
  (A) providing the user with a login prompt;
  (B) accepting the user login input; and
  (C) processing the user login input;
(II) allowing the user to log off said medical imaging system; and further wherein said notifying the user that said analysis is complete can occur either when the user is logged on or when the user is logged off the system.

7. The process of claim 1 wherein:
(I) said providing the user with a set of system options for processing said medical image further includes the option of allowing a user to choose a user information update request; and
(II) further comprising the step of performing a user information update request if the user selected said user information update request.

8. The process according to claim 1 wherein said medical image file is transferred from a user computer over a computer network and further wherein said analysis result is transferred to the user computer over the computer network.

9. The process according to claim 8 wherein said computer network is a Wide Area Network.

10. The process according to claim 8 wherein said computer network is the Internet.

11. A process of providing a computerized medical image analysis system comprising the steps of:
(I) prompting a user to select a system option, said prompting comprising the steps of:
  (A) providing the user with a set of system options for processing said medical image, said system options comprising:
    (i) an image analysis request;
    (ii) an analysis results retrieval request;
    (iv) an image re-analysis request; and
    (iii) a user information update request;
  (B) requesting that the user select at least one of said system options; and
  (C) accepting said user selected system option;
(II) analyzing a medical image file if the user selected said image analysis request, said analyzing comprising the steps of:
  (A) requesting that the user provide medical image information, said image information comprising:
    (i) a location of a medical image file;
    (ii) a job identifier for said image; and
    (iii) processing parameters for processing said image; and
  (B) processing said medical image information, said processing comprising the steps of:
    (i) saving said medical image information in a database;
    (ii) transferring said medical image file to the database, wherein said medical image file is obtained from said location of said medical image file; and
    (iii) linking said medical image parameters and said medical image file to said job identifier;
  (C) analyzing said medical image file, said analyzing comprising the steps of:
    (i) transforming said image file, wherein said transforming creates a transformed image file;
    (ii) storing said transformed image file in said database, wherein said transformed image file is linked to said job identifier;
    (iii) generating an analysis report, wherein said analysis report contains a medical interpretation of said transformed image file;
    (iv) storing said analysis report in said database wherein said analysis report is linked to said job identifier;
    (v) generating a re-run report, wherein said re-run report contains suggested modifications to said processing parameters for a re-analysis of said medical image file; and
    (vi) storing said re-run report in said database, wherein said re-run report is linked to said job identifier; and
  (D) notifying the user that said analysis is complete, wherein said notification can occur either when the user is logged on or when the user is logged off;
(III) transferring an analysis to the user if the user selected said analysis results retrieval request, said transferring comprising the steps of:
  (A) requesting analysis transfer information from the user, said analysis transfer information comprising:
    (i) a job identifier;
    (ii) an transfer location;
    (iii) an transfer option list, said transfer option list comprising:
      (a) an analysis report file transfer option;
      (b) a transformed image file transfer option,
      (c) a view transformed image option; and
      (d) a view analysis report option;
  wherein the user can select one or more transfer options from said transfer option list;
  (B) accepting said analysis transfer information provided by the user, wherein said transfer information is saved in the database linked to said job identifier;
  (C) performing the requested analysis transfer, said performing comprising the steps of:
    (i) transferring said analysis report file to the transfer location if the user selected said analysis report file transfer option;

(ii) transferring said transformed image file to the transfer location if the user selected said transformed image file transfer option;
(iii) sending said transformed image to the user for display if the user selected said view transformed image option;
(iv) sending said analysis report to the user for display if the user selected said view analysis report option; and
(D) notifying the user of a suggested re-analysis of said medical image file if said re-run report recommends a re-analysis;
(IV) re-analyzing said medical image file if the user selected said re-analysis request, said re-analysis comprising the steps of:
(A) prompting the user for the job identifier of the medical image to be re-analyzed;
(B) accepting the updated job identifier input by the user;
(C) prompting the user for an update to said processing parameters;
(D) accepting the updated processing parameters from the user;
(E) re-processing said medical image information, said re-processing comprising the steps of:
(i) linking said medical image parameters and said medical image file to an updated job identifier; and
(ii) linking said updated job identifier to said user ID;
(F) re-analyzing said medical image file, wherein said re-analysis generates analysis results; and
(G) notifying the user that said re-analysis is complete, wherein said notifying can occur either when the user is logged on or when the user is logged off. and
(V) performing a user information update request if the user selected said user information update request.

12. A process according to claim 11 further comprising the steps of:
(I) logging in a user, said login comprising the steps of:
(A) processing a user login request, said login request comprising the steps of:
(i) providing the user with a login prompt;
(ii) accepting a user login input, said login input comprising:
(a) a user ID; and
(b) a user password; and
(iii) processing the user login input, said processing comprising the steps of:
(a) comparing said user ID against a verified user list, wherein the user is prohibited from access to the system if said user ID is not on said verified user list; if said user ID is verified, then:
(b) comparing said user password against a stored password corresponding to said user ID, wherein the user is prohibited from access to the system if said password does not match said password corresponding to said user ID; if said user password is verified then:
(c) permitting user access to the system; and
(iv) preventing the user not verified from accessing system features; and
(II) allowing the user to log off said medical imaging system.

13. The process according to claim 11 wherein said medical image file is transferred from a user computer over a computer network and further wherein said analysis result is transferred to the user computer over the computer network.

14. The process according to claim 13 wherein said computer network is a wide area network.

15. The process according to claim 13 wherein said computer network is the Internet.

16. A process of providing a computerized medical image analysis system comprising the steps of:
(I) connecting a user computer to the system over a computer network;
(II) logging in the user computer, said login comprising the steps of:
(A) processing a user login request, said login request comprising the steps of:
(i) providing the user with a login prompt;
(ii) accepting a user login input, said login input comprising:
(a) a user ID; and
(b) a user password; and
(iii) processing the user login input, said processing comprising the steps of:
(a) comparing said user ID against a verified user list, wherein the user is prohibited from access to the system if said user ID is not on the verified user list; if said user ID is verified, then:
(b) comparing said user password against a stored password corresponding to said user ID, wherein the user is prohibited from access to the system if said password does not match said password corresponding to said user ID; if said user password is verified then:
(c) permitting user access to the system;
(iv) preventing the user not verified from accessing system features; and
(B) providing the user with a set of system options for processing said medical image, said system options comprising:
(i) an image analysis request;
(ii) an analysis result transfer request;
(iv) an image re-analysis request; and
(iii) a user information update request;
(C) requesting that the user select at least one of said system options; and
(D) accepting said user selected system option, wherein said user selected system option is stored in said database;
(III) analyzing a medical image file if the user selected said image analysis request, said analyzing comprising the steps of:
(A) requesting that the user provide medical image information, said image information comprising:
(i) a location of a medical image file;
(ii) a job identifier for said image; and
(iii) processing parameters for processing said image;
(B) processing said medical image information, said processing comprising the steps of:
(i) saving said medical image information in a database;
(ii) transferring said medical image file to said database, wherein said medical image file is obtained from said location of said medical image file;
(iii) linking said medical image parameters and said medical image file to said job identifier; and
(iv) linking said job identifier to said user ID;
(C) analyzing said medical image file, said analyzing comprising the steps of:

(i) transforming said image file, wherein said transforming creates a transformed image file;
(ii) storing said transformed image file in said database, wherein said transformed image file is linked to said job identifier;
(iii) generating an analysis report, wherein said analysis report contains a medical interpretation of said transformed image file; and
(iv) storing said analysis report in said database wherein said analysis report is linked to said job identifier, wherein said analysis report may include a re-run report containing suggested modifications to said processing parameters for a re-analysis of said medical image file if said analysis determines that a re-analysis would be beneficial; and
(D) notifying the user that said analysis is complete, wherein said notification can occur either when the user is logged on or when the user is logged off;
(IV) transferring an analysis result to the user if the user selected said analysis result transfer request, said transferring comprising the steps of:
(A) requesting analysis transfer information from the user, said analysis transfer information comprising:
(i) a job identifier;
(ii) a transfer location;
(iii) a transfer option list, said transfer option list comprising:
(a) a view transformed image option;
(b) a transformed image file transfer option,
(c) a view analysis report option; and
(b) an analysis report file transfer option;
wherein the user can select one or more analysis result transfer options from the transfer option list;
(B) accepting the analysis result transfer information provided by the user,
wherein said transfer information is saved in the database linked to said job identifier;
(C) performing the requested analysis result transfer, said transfer comprising the steps of:
(ii) transferring the analysis report file to the transfer location if the user selected said analysis report file transfer option;
(iii) transferring the transformed image file to the transfer location if the user selected said transformed image file transfer option;
(iv) sending said transformed image to the user for display if the user selected said view transformed image option; and
(v) sending said analysis report to the user for display if the user selected said view analysis report option; and
(D) notifying the user of a suggested re-analysis of said medical image file if said re-run report recommends a re-analysis;
(V) re-analyzing said medical image file if the user selected said re-analysis request, said re-analysis comprising the steps of:
(A) prompting the user for the job identifier of the medical image to be re-analyzed;
(B) accepting the updated job identifier input by the user;
(C) prompting the user for an update to said processing parameters, wherein said prompting may include an option to use suggested parameters obtained during the initial analysis if such parameters were generated;
(D) accepting the updated processing parameters from the user;
(E) re-processing said medical image information, said re-processing processing comprising the steps of:
(i) linking said medical image parameters and said medical image file to an updated job identifier; and
(ii) linking said updated job identifier to said user ID;
(F) analyzing said medical image file; and
(G) notifying the user that said re-analysis is complete, wherein said notification can occur either when the user is logged on or when the user is logged off;
(VI) performing a user information update request if the user selected said user information update request; and
(VII) allowing the user to log off said medical imaging system.

17. A computerized medical image analysis system comprising:
(I) means for prompting a user to select a system option, said prompting means comprising:
(A) means for providing the user with a set of system options for processing said medical image, said system options comprising:
(i) an image analysis request; and
(ii) an analysis results retrieval request;
(B) means for requesting that the user select at least one of said system options; and
(C) means for accepting said user selected system options;
(II) means for analyzing a medical image file if the user selected said image analysis request, said analyzing means comprising:
(A) means for requesting that the user provide medical image information, said image information comprising:
(i) a location of a medical image file;
(ii) a job identifier; and
(iii) processing parameters for analyzing said image file;
(B) means for processing said medical image information, said processing means comprising:
(i) means for saving said medical image information in a database; and
(ii) means for transferring said medical image file to said database, wherein said medical image file is obtained from said location of said medical image file;
(C) means for analyzing said medical image file, said analyzing means comprising:
(i) means for transforming said image file, wherein said transforming creates a transformed image file;
(ii) means for storing said transformed image file in said database, wherein said transformed image file is linked to said job identifier;
(iii) means for generating an analysis report, wherein said analysis report contains a medical interpretation of said transformed image file;
(iv) means for storing said analysis report in said database wherein said analysis report is linked to said job identifier; and
(D) means for notifying the user that said analysis is complete;
(III) means for transferring analysis results to the user if the user selected said analysis results retrieval request, said transferring means comprising:
(A) means for requesting analysis results retrieval transfer information from the user, said analysis results retrieval transfer information comprising:

(i) a job identifier; and
(ii) an transfer options list, wherein the user can select one or more transfer options from said transfer options list;
(B) means for accepting the analysis results retrieval transfer information provided by the user;
(C) means for performing an analysis results transfer to the user.

18. A computerized medical image analysis system according to claim 17 further comprising:
(I) means for processing a user login request, said login means comprising:
(A) means for providing the user with a login prompt;
(B) means for accepting a user login input; and
(C) means for processing the user login input;
(II) means for allowing the user to log off said medical imaging system; and further wherein
said notifying the user that said analysis is complete can occur either when the user is logged on or when the user is logged off the system.

19. A computerized medical image analysis system according to claim 17 wherein:
(I) said analyzing means of said medical image file further comprises:
(A) means for generating a re-run report, wherein said re-run report contains suggested modifications to said processing parameters for a re-analysis of said medical image file; and
(B) means for storing said re-run report in said database, wherein said re-run report is linked to said job identifier;
(II) said means for providing the user with a set of system options for processing said medical image further comprises means for notifying the user of a suggested re-analysis of said medical image file if said re-run report recommends a re-analysis.
(III) said means for providing the user with a set of system options for processing said medical image further comprises an image re-analysis request; and further comprising:

(IV) means for re-analyzing said medical image file if the user selected said re-analysis request, said re-analyzing means comprising:
(A) means for prompting the user for the job identifier of the medical image to be re-analyzed;
(B) means for accepting the updated job identifier input by the user;
(C) means for prompting the user for an update to said processing parameters;
(D) means for accepting the updated processing parameters from the user;
(E) means for re-processing said medical image information, said re-processing means comprising:
(i) means for linking said medical image parameters and said medical image file to an updated job identifier; and
(ii) means for linking said updated job identifier to said user ID;
(F) means for analyzing said medical image file; and
(G) means for notifying the user that said re-analysis is complete; and
(V) means for transferring re-analysis results to the user if the user selected said analysis results retrieval request.

20. A computerized medical image analysis system according to claim 19 further comprising:
(I) means for processing a user login request, said login request means comprising:
(A) means for providing the user with a login prompt;
(B) means for accepting a user login input; and
(C) means for processing the user login input;
(II) means for allowing the user to log off said medical imaging system; and further
wherein said notifying the user that said analysis is complete can occur either when the user is logged on or when the user is logged off the system.

* * * * *